(12) United States Patent
Barth et al.

(10) Patent No.: US 6,740,768 B1
(45) Date of Patent: May 25, 2004

(54) METHOD FOR PRODUCING SYMMETRICAL AND ASYMMETRICAL CARBONATES

(75) Inventors: Hubert Barth, Emmendingen (DE); Klaus Steiner, Emmendingen (DE); Simon Schneider, Merzhausen (DE); Ulrich Bayer, Ulm (DE); Manfred Westermayer, Gundelfingen (DE); Ulrike Wolfsperger, Gundelfingen (DE)

(73) Assignee: Goedecke GmbH (DE)

( * ) Notice: Subject to any disclaimer, the term of this patent is extended or adjusted under 35 U.S.C. 154(b) by 0 days.

(21) Appl. No.: 09/869,871

(22) PCT Filed: Jan. 18, 2000

(86) PCT No.: PCT/EP00/00340

§ 371 (c)(1), (2), (4) Date: Jul. 22, 2002

(87) PCT Pub. No.: WO00/47544

PCT Pub. Date: Aug. 17, 2000

(30) Foreign Application Priority Data

Feb. 9, 1999 (DE) ......................... 199 05 222

(51) Int. Cl.$^7$ .............................................. C07C 68/04
(52) U.S. Cl. ..................................... 558/260; 558/275
(58) Field of Search .................................. 558/260, 275

(56) References Cited

FOREIGN PATENT DOCUMENTS

JP 7033715 2/1995

OTHER PUBLICATIONS

Fang and Fujimoto, "Direct synthesis of dimethyl carbonate from carbon dioxide and methanol catalyzed by base", *Appl. Catal.*, vol. 142, No. 1, 1996, pp. L1–L3.

Butcher, "Carbamate esters: a simple, mild method of formation", *Synlett*, 1994, pp 825–826.

Database WPI, Section CH, Week 199515, Derwent Publications Ltd., London, GB, AN 1995–110592.

*Primary Examiner*—Joseph K. McKane
*Assistant Examiner*—Kamal Saeed
(74) *Attorney, Agent, or Firm*—Charles W. Ashbrook; Matthew J. Russo

(57) ABSTRACT

Process for the preparation of symmetrical and asymmetrical carbonates of the general formula I

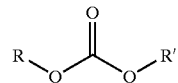

I by reaction of alcohols of the general formula II and alkyl or aryl halides of the general formula III,

R—OH     II

R'—HAL     III with carbon dioxide and caesium carbonate at room temperature in dipolar aprotic solvents.

5 Claims, No Drawings

METHOD FOR PRODUCING SYMMETRICAL AND ASYMMETRICAL CARBONATES

The present invention concerns the preparation of symmetrical and asymmetrical carbonates of the general formula I

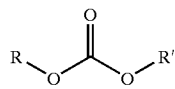

I wherein R and R' are the same or different and signify a straight-chained or branched alkyl group with 1 to 10 C-atoms, a benzyl group unsubstituted or substituted with up to three $C_1$–$C_4$-alkyl groups, $C_1$–$C_4$-alkoxy groups, halogen atoms, with a cyano group, a nitro group, a trifluoromethyl group or an alkoxycarbonyl group with up to 4 C-atoms, an aralkyl group or an alkenyl group. The term aralkyl group includes a lower alkyl radical with 2 to 10 C-atoms, wherein up to two H atoms are replaced by phenyl groups, which again can be substituted with a $C_1$–$C_4$-alkyl group, a $C_1$–$C_4$-alkoxy group, a cyano group, a nitro group, a trifluoromethyl group, an alkoxycarbonyl group with up to 4 C-atoms or with up to three halogen atoms. The term alkenyl designates an unsaturated hydrocarbon radical with up to 5 C-atoms.

Organic carbonates play an important role as solvents, as intermediate products for numerous syntheses and as products for special fields of use, e.g. in agricultural chemistry or medicinal chemistry (Ullmann's Encyclopedia of Industrial Chemistry, 5th edition, Vol. A5, p. 197, 1986; KIRK-OTHMER, Encyclopedia of Chemical Technology, 3rd ed., Vol. 4, p. 766, 1978; Abbas-Alli G. Shaikh, Chem. Rev. 1996, 96, 951–976).

The preparation of open-chained organic carbonates can e.g. take place (i) from phosgene and hydroxy compounds, (ii) from haloformic acids by reaction with hydroxy compounds, (iii) by alkylation of alkali metal carbonates, (iv) by transesterification of carbonic acid diesters or (v) from carbon dioxide and alcohols under pressure in the presence of catalysts or, however, according to other special processes (H. Hagemann, HOUBEN WEYL, E4, p. 65, 1983; Abbas Alli G. Shaikh, Chem. Rev. 1966, 96, 951).

Processes for the preparation of organic carbonates which avoid the use of the highly toxic phosgene which can use carbon dioxide present and start from simple raw materials are of especial interest from industrial as well as organic-preparative point of view. Stimulated by a work of Ken J. Butcher for the preparation of carbamates from amines and carbon dioxide (Ken J. Butcher, Synlett 1994, 825), it was investigated by us whether alcohols of the general formula II, with use of carbon dioxide, caesium. carbonate and alkyl or aryl halides of the general formula III,

 R—OH        II

 R'—HAL      III whereby R and R' possess the above mentioned meaning and HAL stands for chlorine, bromine or iodine, can be converted into organic carbonates of the general formula I (scheme 1):

On the basis of the lower nucleophilia of the OH group in alcohols in comparison with the $NH_2$ group in amines and on the basis of the special methods described in the literature for the preparation of carbonates from carbon dioxide (Abbas-Alli G. Shaikh, Chem. Rev. 1996, 951, 966), a synthetic access to carbonates with use of the system carbon dioxide/caesium carbonate at low temperatures was not to be expected.

Surprisingly, however, it was found that organic carbonates of the general formula I can be prepared under very mild and preparatively simple conditions in the presence of alkali metal carbonates, especially caesium carbonate, from alcohols of the general formula II and alkyl or aryl halies of the general formula III. For this reaction, surprisingly no further catalyst is necessary. The preparative procedure is as follows:

The alcohol and a 2 to threefold molar excess of caesium carbonate are placed in a suitable dipolar aprotic solvent, such as e.g. dimethylformamide, acetonitrile, dimethylacetamide or N-methylpyrrolidone, at room temperature. With good stirring, carbon dioxide gas is now passed at room temperature, with exclusion of moisture, for 4 to 6 hours into the reaction mixture (about 5 bubbles/second). The carbon dioxide is hereby produced by allowing dry ice to evaporate which is present in an Erlenmeyer flask which is connected with the reaction vessel via a gas inlet pipe. One now adds to the reaction mixture in one portion 1 equivalent (referred to the alcohol) of the alkyl or aryl halide in question of the general formula III, dissolved in a little solvent, passes further carbon dioxide in for 1 hour, again adds thereto 5–100%, preferably 10%, of the original amount of alkyl or aryl halide and then closes the reaction vessel. With closed reaction vessel, one now stirs further for 24 hours to 3 days at room temperature. Thereafter, one pours the reaction mixture on to water, extracts the product with ethyl acetate and purifies the so obtained raw product with the methods usual in preparative organic chemistry, e.g. by chromatography or crystallisation. Preferred solvent for the described reaction is dimethylformamide.

The reaction conditions are very mild, there are tolerated many functional groups, such as e.g. the double bond, the nitro group, the alkoxycarbonyl group, the cyano group, halogen groups and alkoxy groups on aromatics. The starting materials—alcohols and alkyl and aryl halies—are simple to prepare and are commercially available in large number. The conditions for the working up of the reaction are very easy to produce. With the assumption that caesium carbonate can again be prepared from the extracted aqueous residue, the method is suitable to bind gaseous carbon dioxide on to simple commercially available starting materials, such as alcohols and alkyl or aryl halides and thereby to produce valuable, energy-rich intermediate products. In this sense, the said process is a valuable addition to an environmentally friendly chemistry.

Because of the simplicity of the process, the method of procedure is also suitable as basis for a high throughput synthesis. For this purpose, in a carbon dioxide gasification apparatus which contains DMF solutions of corresponding alcohols, would have to be gassed with $CO_2$ for some hours. Thereafter, the corresponding alkyl or aryl halides are to be dosed thereto, the vessel to be closed and to be stirred for 24 hours to 3 days at room temperature. Thereafter, the carbonates formed are to be isolated in simple manner.

The invention is illustrated and explained by the following embodimental Examples.

EXAMPLE 1

Dibenzyl Carbonate From Benzyl Alcohol and Benzyl 5 Bromide

Into a suspension of 0.45 g benzyl alcohol and 3.0 g caesium carbonate in 30 ml dry dimethylformamide, which is present in a 50 ml three-necked flask, carbon dioxide gas is passed for 4 hrs, with good stirring at room temperature. One adds thereto 0.7 g benzyl bromide dissolved in a little DMF, passes in further carbon dioxide for 1 hr., again mixes with 0.1 g benzyl chloride and then closes the reaction vessel airtight. The reaction mixture is now further stirred for 2 days at room temperature. Thereafter, one pours the reaction mixture on to 50 ml water (care: exothermic reaction) and extracts the product 3 times with, in each case, 50 ml ethyl acetate. The organic phase is dried over sodium sulphate, filtered and evaporated on a rotavapor. The dimethylformamide present in the oily residue, together with the product, is removed on the rotavapor by azeotropic distillation by means of toluene at 40 mbar/50° C. The residue is chromatographed on 130 g silica gel (0.040–0.063) with toluene as elution agent. One obtains 0.95 g of product. M.p. 30–31° C.

The following Examples are carried out analogously to Example 1 (reaction time in hours/yield):

EXAMPLE 2

Benzyl 2-phenylethyl carbonate, oil from 2-phenylethanol and benzyl bromide 48/93%

EXAMPLE 3

Benzyl ethyl carbonate, oil, from benzyl alcohol and ethyl bromide 18/73.%

EXAMPLE 4

Benzyl tert.-utyl carbonate, oil, from tert.-butanol and benzyl bromide 120/15%

EXAMPLE 5

Di-Benzo[b]furan-2-yl methyl carbonate, oil, from 2-hydroxymethylbenzo[b]furan 120/23%

EXAMPLE 6

Benzyl 3-phenylpropyl carbonate, oil, from 3-phenylpropanol and benzyl bromide 120/99%

EXAMPLE 7

Benzyl 4-chlorobenzyl carbonate, oil, from benzyl alcohol and 4-chlorobenzyl chloride 64/50%

EXAMPLE 8

Benzyl 4-methoxybenzyl carbonate, oil, from benzylalcohol and 4-methoxybenzyl chloride 88/64.4%

EXAMPLE 9

Benzyl 4-methylbenzyl carbonate, oil, from benzyl alcohol and 4-methylbenzyl chloride 64/52.3%

EXAMPLE 10

Benzyl 2,4-dichlorobenzyl carbonate, oil, from benzyl alcohol and 2,4-dichlorobenzyl chloride 64/49%

EXAMPLE 11

4–Chlorobenzyl 2-phenylethyl carbonate, oil, from 2-phenylethanol and 4-chlorobenzyl chloride 64/32.7%

EXAMPLE 12

Di-4-methoxybenzyl carbonate, m.p. 73° C., from 4-methoxybenzyl alcohol and 4-methoxybenzyl chloride 88/72%

EXAMPLE 13

Di-2,4-dichlorobenzyl carbonate, oil, from 2,4-dichlorobenzyl alcohol and 2,4-dichlorobenzyl chloride 64/70.5%

EXAMPLE 14

Di-4-methylbenzyl carbonate, m.p. 55° C., from 4-methylbenzyl alcohol and 4-methylbenzyl bromide 88/40%

EXAMPLE 15

Di-4-chlorobenzyl carbonate, m.p. 94° C., from 4-chlorobenzyl alcohol and 4-chlorobenzyl bromide 64/78.3%

EXAMPLE 16

Di-4-chlorobenzyl carbonate, m.p. 97° C., from 4-chlorobenzyl alcohol and 4-chlorobenzyl chloride 64/54.8%

EXAMPLE 17

(±)-Benzyl-2-methyl-2-phenylethyl carbonate, oil, from (±)-2-methyl-2-phenylethyl alcohol and benzyl bromide 64/63.1%

EXAMPLE 18

Benzhydryl benzyl carbonate, m.p. 72° C., from benzhydrol and benzyl bromide 64/71.2%

EXAMPLE 19

(±)-Benzyl 1-phenylethyl carbonate, oil, from (±)-1-phenylethanol and benzyl bromide 64/57.1%

EXAMPLE 20

Benzyl 3-phenylpropyl carbonate, oil, from 3-phenylpropanol and benzyl bromide 120/99%

EXAMPLE 21

(±)-Benzyl 1-methyl-2-phenylethyl carbonate, oil, from (±)-1-phenyl-2-propanol and benzyl bromide 120/99%

EXAMPLE 22

Benzyl 4-methoxycarbonylbenzyl carbonate, m.p. 53° C., from 4-methoxycarbonylbenzyl alcohol and benzyl bromide 120/65%

EXAMPLE 23

Di-4-nitrobenzyl carbonate, m.p. 167°–168° C., from 4-nitrobenzyl alcohol and 4-nitrobenzyl bromide 64/77%

EXAMPLE 24

Benzyl benzo[b]furan-2-ylmethyl carbonate, m.p. 59°–60° C., from 2-hydroxymethylbenzo[b]furan and benzyl bromide 64/100%

EXAMPLE 25

Benzyl 4-cyanobenzyl carbonate, m.p. 54° C., from benzyl alcohol and 4-cyanobenzyl bromide 64/100%

EXAMPLE 26

Benzyl 3-trifluoromethylbenzyl carbonate, oil, from benzyl alcohol and 3-trifluoromethylbenzyl bromide 48/100%

EXAMPLE 27

Benzyl 1-phenylethyl carbonate, oil, from benzyl alcohol and 1-phenylethyl bromide 64/66%

EXAMPLE 28

Di-2-phenylethyl carbonate, m.p. 56° C., from 2-phenylethanol and 2-phenylethyl bromide 64/69.4%

EXAMPLE 29

Di-3-phenylpropyl carbonate, oil, from 3-phenylpropanol and 3-phenylpropyl bromide 64/98%

EXAMPLE 30

Benzyl tert.-utyl carbonate, oil, from benzyl alcohol and tert.-utyl bromide 64/7%

EXAMPLE 31

Benzyl 4-Nitrobenzyl carbonate, m.p. 68° C., from benzyl alcohol and 4-nitrobenzyl bromide 64/93%

EXAMPLE 32

Allyl benzyl carbonate, oil, from benzyl alcohol and allyl bromide 64/80%

EXAMPLE 33

Allyl benzyl carbonate, oil, from allyl alcohol and benzyl bromide 64/70%

EXAMPLE 34

Benzyl cinnamyl carbonate, oil, from cinnamyl alcohol and benzyl bromide 64/74.5%

EXAMPLE 35

(±)-Benzyl 1-methylpropyl carbonate, oil, from (±)-1-methylpropanol and benzyl bromide 64/58%

EXAMPLE 36

Benzyl butyl carbonate, oil, from n-butanol and benzyl bromide 48/58.5%

EXAMPLE 37

Benzyl 4-nitrobenzyl carbonate, m.p. 68° C, from 4-nitrobenzyl alcohol and benzyl bromide 64/80.6%.

What is claimed is:

1. Process for the preparation of symmetrical and asymmetrical carbonates of the general formula I

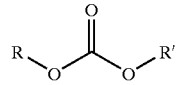

in which R and R' are the same or different and signify a straight-chained or branched alkyl group with 1 to 10 C-atoms, a benzyl group unsubstituted or substituted with up to three $C_1$–$C_4$-alkyl groups, $C_1$–$C_4$-alkoxy groups, halogen atoms, with a cyano group, a nitro group, a trifluoromethyl group or an alkoxycarbonyl group with up to 4 C-atoms, characterised in that one converts alcohols of the general formula II and alkyl or aryl halides of the general formula III $$R\text{—OH} \qquad \text{II}$$

$$R'\text{—HAL} \qquad \text{III}$$

in which R and R' possess the above-given meaning and HAL stands for chlorine, bromine or iodine, by reaction with carbon dioxide and caesium carbonate in a dipolar aprotic solvent into organic carbonates of the general formula I.

2. Process according to claim 1, characterised in that the solvent is dimethylformamide, acetonitrile, dimethylacetamide or N-methylpyrrolidone.

3. Process according to claim 1, characterised in that the reaction is carried out at room temperature.

4. Process according to claim 1, characterised in that the carbon dioxide is passed gaseous into the reaction batch.

5. Process according to claim 1, characterised in that the alcohol (II) is placed with a 2 to 3 fold excess of caesium-.carbonate in a polar aprotic solvent, carbon dioxide gas is passed in for several hours and subsequently the halide (III) is added in equimolar amount and the passing in of carbon dioxide gas is continued for some time.

\* \* \* \* \*